(12) United States Patent
Elokdah et al.

(10) Patent No.: US 6,562,814 B2
(45) Date of Patent: May 13, 2003

(54) 3-THIOXO-[1,2,4]-OXADIAZINAN-5-ONE DERIVATIVES

(75) Inventors: Hassan M. Elokdah, Yardley; Theodore S. Sulkowski, Wayne, both of PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/965,874

(22) Filed: Sep. 28, 2001

(65) Prior Publication Data

US 2002/0061883 A1 May 23, 2002

Related U.S. Application Data

(60) Provisional application No. 60/237,468, filed on Oct. 2, 2000.

(51) Int. Cl.[7] .................. A61K 31/535; C07D 273/04
(52) U.S. Cl. ................................. 514/229.2; 544/268
(58) Field of Search ................. 544/68; 514/229.2

(56) References Cited

U.S. PATENT DOCUMENTS

| | | | |
|---|---|---|---|
| 3,438,985 A | | 4/1969 | Berstein |
| 3,537,839 A | * | 11/1970 | Steinbrunn et al. ........... 544/68 |
| 3,625,968 A | * | 12/1971 | Zschocke et al. ............. 544/68 |
| 3,696,099 A | * | 10/1972 | Makula et al. ............... 544/68 |
| 5,861,517 A | | 1/1999 | Elokdah .................. 548/321.1 |

FOREIGN PATENT DOCUMENTS

| | | |
|---|---|---|
| FR | 1432738 | 3/1966 |
| WO | WO 97/32855 | 9/1997 |
| WO | WO 98/21190 | 5/1998 |

OTHER PUBLICATIONS

Golfman et al, Circulation, 34, 1966, 679–697.
Miller and Miller, Lancet, 1, 1975, 16–19.
Gordon et al, Circulation, 79, 1989, 8–15.
Stampfer et al, N. Engl. J. Med., 325, 1991, 373–381.
Badimon et al, Lab. Invest., 60, 1989, 455–461.
Miller et al, Br. Med. J., 282, 1981, 1741–1744.
Picardo et al, Arteriosclerosis, 6, 1986, 434–441.
Glomset, J. Lipid Res., 9, 1968, 155–167.
Glass et al, J. Biol. Chem., 258, 1983, 7161–7167.
MacKinon et al, J. Biol. Chem., 261, 1986, 2548–2552.
Grow and Fried, J. Biol. Chem., 253, 1978, 1834–1984.
Lagocki and Scanu, J. Biol. Chem., 255, 1980, 370–3706.
Schaefer et al, J. Lipids Res., 23, 1982, 1259–1273.
Berkowitz, Phillip T. et al, J. Org. Chem., 41, 1976, 3128.
Berkowitz, Phillip T. et al, J. Med. Chem., 20, 1977, 134.

\* cited by examiner

Primary Examiner—John M. Ford
(74) Attorney, Agent, or Firm—Michael R. Nagy

(57) ABSTRACT

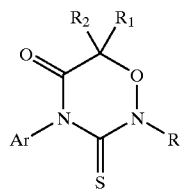

wherein

R is alkyl, alkenyl, or alkynyl;

$R_1$ and $R_2$ are each independently hydrogen alkyl, or aryl; and

Ar is phenyl, indanyl, benzhydryl, or phenyl, substituted with one or more groups selected from the group consisting of halogen, alkyl, perfluoroalkyl, lower alkoxy, perfluoroalkylalkoxy, dialkylamino, and aroyloxy.

15 Claims, No Drawings

3-THIOXO-[1,2,4]-OXADIAZINAN-5-ONE DERIVATIVES

This application claims priority from copending provisional application Ser. No. 60/237,468, filed Oct. 2, 2000, the entire disclosure of which is hereby incorporated by reference.

FIELD OF THE INVENTION

This invention is directed to anti-atherosclerotic agents and more specifically, to compounds, compositions and methods for treating atherosclerotic conditions, such as dyslipoproteinemias and coronary heart disease. This invention specifically relates to 3-thioxo-[1,2,4]-oxadiazinan-5-one derivatives that elevate HDL cholesterol concentration, and which may be useful for the treatment of atherosclerotic conditions such as coronary heart disease.

BACKGROUND OF THE INVENTION

Numerous studies have demonstrated that both the risk of coronary heart disease (CHD) in humans and the severity of experimental atherosclerosis in animals are inversely correlated with serum HDL cholesterol (HDL-C) concentrations (Ross et al, *Am. J. Med.*, 11 (1951) 480–493; Gofman et al, *Circulation*, 34 (1966) 679–697; Miller and Miller, *Lancet*, 1 (1975) 16–19; Gordon et al, *Circulation*, 79 (1989) 8–15; Stampfer et al, *N. Engl. J. Med.*, 325 (1991) 373–381; Badimon et al, *Lab. Invest.*, 60 (1989) 455–461). Atherosclerosis is the process of accumulation of cholesterol within the arterial wall which results in the occlusion, or stenosis, of coronary and cerebral arterial vessels and subsequent myocardial infarction and stroke. Angiographical studies have shown that elevated level of some HDL particles in humans appears to be correlated to a decreased number of sites of stenosis in the coronary arteries of humans (Miller et al, *Br. Med. J.*, 282 (1981) 1741–1744).

There are several mechanisms by which HDL may protect against the progression of atherosclerosis. Studies in vitro have shown that HDL is capable of removing cholesterol from cells (Picardo et al, *Arteriosclerosis*, 6 (1986) 434–441). Data of this nature suggest that one antiatherogenic property of HDL may lie in its ability to deplete tissues of excess free cholesterol and eventually lead to the delivery of this cholesterol to the liver (Glomset, *J. Lipid Res.*, 9 (1968) 155–167). This has been supported by experiments showing efficient transfer of cholesterol from HDL to the liver (Glass et al, , *J. Biol. Chem.*, 258 (1983) 7161–7167; MacKinnon et al, *J. Biol. Chem.*, 261 (1986) 2548–2552). In addition, HDL may serve as a reservoir in the circulation for apoproteins necessary for the rapid metabolism of triglyceride-rich lipoproteins (Grow and Fried, *J. Biol. Chem.*, 253 (1978) 1834–1841; Lagocki and Scanu, *J. Biol. Chem.*, 255 (1980) 3701–3706; Schaefer et al, *J. Lipid Res.*, 23 (1982) 1259–1273). Accordingly, agents which increase HDL cholesterol concentrations are useful as anti-atherosclerotic agents, particularly in the treatment of dyslipoproteinemias and coronary heart disease.

U.S. Pat. No. 3,438,985 discloses a process for preparing 1,2,4-oxadiazinan-3,5-diones, useful as anticonvulsants.

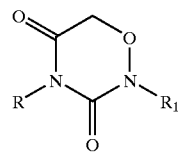

wherein R and $R_1$ represent hydrogen and alkyl. Preferred compounds are those where $R_1$ represents hydrogen and R represents hydrogen or lower alkyl.

U.S. Pat. No. 3,625,968 discloses the production of 1,2,4-oxadiazinan-3,5-diones useful as herbicides, diuretics and antiphlogistic pharmaceuticals,

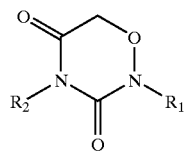

wherein $R_1$ and $R_2$ may be different or identical and each denotes an aliphatic, araliphatic, cycloaliphatic or aromatic group. $R_1$ may also be hydrogen and $R_2$ may also denote arylsulfonyl radical or heterocyclic radical.

French Patent No. 1,432,738 also discloses a process for the preparation of 1,2,4-oxadiazinan-3,5-diones according to the following formula:

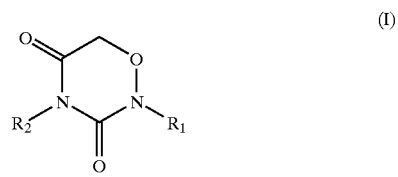

wherein $R_1$ and $R_2$ are hydrogen, alkyl, cycloalkyl, aryl, or aralkyl, same or different, the aryls optimally substituted by alkyl, halogen, nitro or amino.

The preparation of 5-thioxo-1,2,4-oxadiazinan-3-ones by treatment of 1,2,4-oxadiazin-3,5-diones with phosphorus pentasulfide is cited in Berkowitz, Phillip T. et al., *J. Org. Chem.*, 41, 3128 (1976) and *J. Med. Chem.*, 20, 134 (1977). These compounds are used as intermediates in the preparation of 5-substituted amino-1,2,4-oxadiazin-3-ones useful as antibacterial agents.

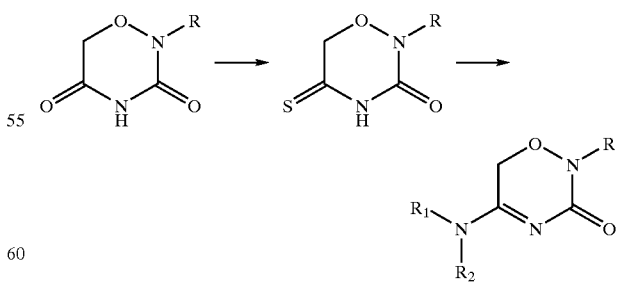

SUMMARY OF THE INVENTION

In accordance with this invention there are provided substituted 3-thioxo 1,2,4-oxadiazin-5-ones of Formula I:

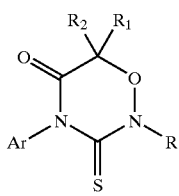

(I)

wherein

R is lower alkyl, alkenyl of 2–6 carbon atoms, or alkynyl of 2–6 carbon atoms;

$R_1$ and $R_2$ are each independently hydrogen alkyl, or aryl; and

Ar is phenyl, indanyl, benzhydryl, or phenyl substituted with one or more members of the group selected from the group consisting of halogen, lower alkyl, perfluoroalkyl, lower alkoxy, perfluoroalkylalkoxy, dialkylamino, and aroyloxy; or pharmaceutically acceptable salts thereto.

The present invention also provides methods of treating arteriosclerosis and related coronary heart disease or dyslipoproteinemias and improving the HDL concentration in a mammal in need thereof which comprises administering to the mammal a compound of Formula I:

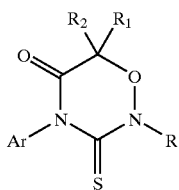

(I)

wherein

R is lower alkyl, alkenyl of 2–6 carbon atoms, or alkynyl of 2–6 carbon atoms;

$R_1$ and $R_2$ are each independently hydrogen alkyl, or aryl; and

Ar is phenyl, indanyl, benzhydryl, or phenyl, substituted with one or more members of the group consisting of halogen, alkyl, perfluoroalkyl, lower alkoxy, perfluoroalkylalkoxy, dialkylamino, and aroyloxy; or pharmaceutical acceptable salts thereof.

DETAILED DESCRIPTION OF THE INVENTION

Preferably, the present compounds are those represented by Formula I:

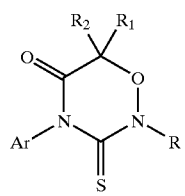

(I)

wherein
R is alkyl;
$R_1$ and $R_2$ are each hydrogen; and
Ar is phenyl, indanyl, benzhydryl, or phenyl substituted with one or more members of the group consisting of halogen, lower alkyl, lower alkoxy, and aroyloxy.

As used herein, the terms "lower alkyl" and "lower alkoxy" are meant to include both straight and branched chain moieties containing 1–6 carbon atoms. The term "aryl" is meant to include aromatic radicals of 6–12 carbon atoms. The term "halogen" is meant to include fluorine, chlorine, bromine and iodine.

The pharmaceutically acceptable salts of the present compounds include those derived from organic and inorganic acids such as acetic, lactic, citric, tartaric, succinic, fumaric, maleic, malonic, mandelic, malic, hydrochloric, hydrobromic, phosphoric, nitric, sulfuric, methanesulfonic, toluene sulfonic, and similarly known acceptable acids.

The most preferred compounds of this invention are:
4-(5-Chloro-2-methylphenyl)-2-methyl-3-thioxo-1,2,4-oxadiazin-5-one;
4-(5-Chloro-2-methylphenyl)-2-ethyl-3-thioxo-1,2,4-oxadiazin-5-one;
4-(4-Chloro-2-methylphenyl)-2-methyl-3-thioxo-1,2,4-oxadiazin-5-one;
4-(Indan-5-yl)-2-methyl-3-thioxo-1,2,4-oxadiazin-5-one;
4-(2,5-Dimethylphenyl)-2-methyl-3-thioxo-1,2,4-oxadiazin-5-one;
4-(6-Chloro-2-methylphenyl)-2-methyl-3-thioxo-1,2,4-oxadiazin-5-one;
4-(2-Isopropylphenyl)-2-methyl-3-thioxo-1,2,4-oxadiazin-5-one;
4-(Diphenylmethyl)-2-methyl-3-thioxo-1,2,4-oxadiazin-5-one;
4-(4-t-Butylylphenyl)-2-methyl-3-thioxo-1,2,4-oxadiazin-5-one;
4-(4-Phenoxyphenyl)-2-methyl-3-thioxo-1,2,4-oxadiazin-5-one; and
4-(5-Chloro-2-methoxyphenyl)-2-methyl-3-thioxo-1,2,4-oxadiazin-5-one.

The compounds of the invention can be readily prepared according to the following reaction scheme or modification thereof using readily available starting materials, reagents and conventional synthetic procedures. It is also possible to make use of variants of these process steps, which in themselves are known to and well within the preparatory skill of the medicinal chemist. In the following reaction scheme R is alkyl, $R_1$ is alkyl, alkenyl, or alkynyl, $R_2$, $R_3$ and $R_4$ are independently hydrogen, halogen, alkyl, alkenyl, etc.

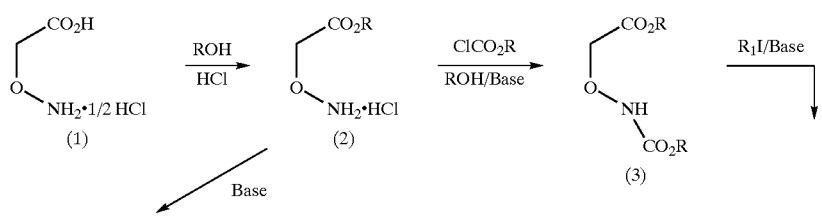

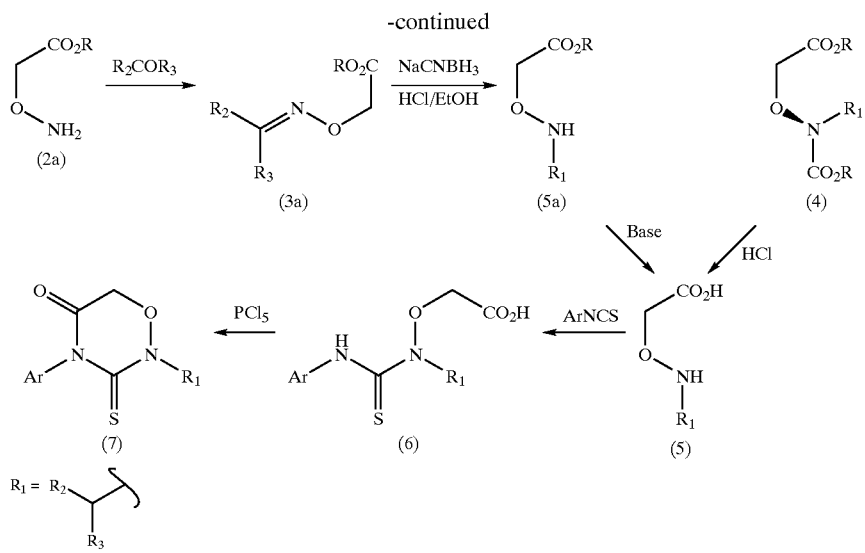

The aminooxy acetate ester hydrochloride (2) was prepared by esterifying carboxymethoxyl amine hemihydrochloride (1) with the appropriate alcohol saturated with hydrogen chloride at ambient temperature for 24 hours. Reaction of 2 at ambient temperature over a period of 3–5 hours with ethyl- or methyl-chloroformate in the presence of base such as sodium bicarbonate and a solvent such as alcohol afforded the oxy-carbamate (3). Alkylation of 3 with alkyl iodides (excess) in refluxing alcohol under basic conditions over a period of 2 to 3 hours afforded 4. Hydrolysis of 4 to the N-alkyl-carboxymethoxylamine hydrochloride (5) was carried out by refluxing with an acid such as hydrochloric acid over 20 minutes to one hour period. Alternatively, ethyl aminoxy acetate (2a) was liberated from its hydrochloride salt with base, reaction of 2a with 2–5 fold excess of aldehydes or ketones either neat or in a alcohol over a period of 1 to 4 hours under reflux afforded the imine (3a). Hydride reduction of 3a under acidic condition in a solvent such as an alcohol followed by basic workup afforded the amine (5a). Saponification of the ester with base followed by acidic workup afforded the corresponding alkylaminoxyacetic acid salt (5). Reaction of 5 with isothiocyanates under basic conditions in a solvent such as chloroform or ether over a period of 20 minutes to 1 hour afforded the thioureidooxyacetic acid (6). Cyclization of 6 to the oxadiazine (7) was carried out by the action of phosphorus pentachloride in refluxing benzene.

The ability of the compounds of this invention to increase blood serum HDL levels was established by the following standard experimental procedure for determination of HDL cholesterol:

Male Sprague-Dawley rats weighing 200–225 g were housed two per cage and fed Purina Rodent Chow Special Mix 5001-S supplemented with 0.25% cholic acid and 1.0% cholesterol and water ad libitum for 8 days. Each test substance is administered to a group of six rats fed the same diet with the test diet mixed in as 0.005–0.1% of the total diet. Body weight and food consumption were recorded prior to diet administration and at termination. Typical doses of the test substances were 5–100 mg/kg/day.

At termination, blood was collected from anesthetized rats and the serum was separated by centrifugation. Total serum cholesterol was assayed using the Sigma Diagnostics enzymatic kit for the determination of cholesterol, Procedure No. 352, modified for use with ninety-six well microtiter plates. After reconstitution with water the reagent contains 300 U/I cholesterol oxidase, 100 U/I cholesterol esterase, 1000 U/I horse radish peroxidase, 0.3 mmoles/l 4-aminoantipyrine and 30.0 mmoles/l p-hydroxybenzenesulfonate in a pH 6.5 buffer. In the reaction cholesterol was oxidized to produce hydrogen peroxide which was used to form a quinoneimine dye. The concentration of dye formed was measured spectrophotometrically by absorbence at 490 nm after incubation at 25° C. for 30 minutes. The concentration of cholesterol was determined for each serum sample relative to a commercial standard from Sigma.

HDL cholesterol concentrations in serum are determined by separation of lipoprotein classes by fast protein liquid chromatography (FPLC) by a modification of the method of Kieft et al., *J. Lipid Res.*, 32 (1991) 859–866. 25 ul of serum was injected onto Superose 12 and Superose 6 (Pharmacia), in series, with a column buffer of 0.05 M Tris (2-amino-2-hydroxymethyl-1,3-propanediol) and 0.15 M sodium chloride at a flow rate of 0.5 ml/min. The eluted sample was mixed on line with Boehringer-Mannheim cholesterol reagent pumped at 0.2 ml/min. The combined eluents are mixed and incubated on line through a knitted coil (Applied Biosciences) maintained at a temperature of 45C. The eluent was monitored by measuring absorbence at 490 nm and gives a continuous absorbence signal proportional to the cholesterol concentration. The relative concentration of each lipoprotein class was calculated as the percent of total absorbence. HDL cholesterol concentration, in serum, was calculated as the percent of total cholesterol as determined by FPLC multiplied by the total serum cholesterol concentration.

Test compounds were administered at the specified dose. Each test substance was administered to a group of six rats. The duration of treatment was eight days. The compounds of the present invention increase HDL cholesterol concentrations is summarized in Table I:

TABLE I

| Compound of Example | Dose (mg/kg/day) | HDL Cholesterol Level Increase (%) |
|---|---|---|
| 1. | 100 | 221 |
| 2. | 100 | 60 |
| 3. | 100 | 236 |
| 4. | 85 | 136 |
| 5. | 100 | 192 |
| 6. | 100 | 72 |
| 7. | 100 | 100 |
| 8. | 100 | 95 |
| 9. | 100 | 170 |
| 10. | 100 | 102 |
| 11. | 100 | 78 |

This invention also provides pharmaceutical compositions comprised of 2-thioxo-1,2,4-oxadiazin-5-ones either alone or in combination with excipients (i.e. pharmaceutically acceptable materials with no pharmacological effects). Such compositions are useful in the treatment of atherosclerotic conditions such as dyslipoproteinemias and coronary heart disease, in that they increase the blood serum high density lipoprotein concentration of mammals treated with the compounds.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid which is in admixture with the finely divided active ingredient. In tablets the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions which are sterile solutions or suspensions can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physician's direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patient's recovery rate. By initiating the treatment regimen with a minimal daily dose of about one gram, the blood levels of HDL and the patients symptomatic relief analysis may be used to determine whether a larger dose is indicated. Based upon the data presented below, the projected daily dose for both human and veterinary use will be from about 25 to about 200 milligrams/kilogram per day, and more usually, from about 50 to about 100 milligrams/kilogram per day.

The following examples are presented to illustrate the production of representative compounds useful in the methods of this invention, rather than as limit to the scope of the invention:

N-SUBSTITUTED AMINOOXY ACETIC ACIDS (5)

Procedure A

Step 1

Ethyl Aminooxy acetate hydrochloride (2, R=Et)

Aminoxyacetic acid hemihydrochloride (500 g) was suspended in ethanol (2000 mL). The mixture was saturated with hydrogen chloride and allowed to stand at room temperature for 24 hours. The mixture was then concentrated to the precipitation point. The solid was collected by filtration, washed with ether and dried to give the title compound as a white solid (547 g), m.p. 115–117° C. Mass spectrum (EI, M.+) m/z 119. $^1$H-NMR (DMSO-$d_6$; 300 MHz): δ11.08 (br s, 3H), 4.74 (s, 2H), 4.16 (q, 2H), and 1.21 ppm (t, 3H).

Anal. for $C_4H_9NO_3$. HCl: Calcd.: C, 30.88; H, 6.48; N, 9.00. Found: C, 30.55; H, 641; N, 9.16.

Step 2

Ethyl N-Ethoxy carbonyl aminooxy acetate (3, R=Et)

The mixture of ethyl Aminooxy acetate hydrochloride (540 g), Sodium bicarbonate (300 g), and ethanol (1700 mL) was vigorously stirred with a mechanical stirrer. Ethyl chloroformate (395 g) was added dropwise. Additional amount of sodium bicarbonate (300 g) was added in portions to keep the reaction mixture basic. The reaction mixture was stirred at ambient temperature for 3 hours. The mixture was then filtered. The solid was rinsed with fresh ethanol. The combined filtrate was evaporated to dryness. The residue was dissolved in ethyl acetate (1500 mL) and washed with water (2×500 mL). The organic phase was dried over anhydrous magnesium sulfate, filtered, and evaporated to an oily residue. The oily residue solidified into a crystalline mass upon standing. The solid mass was crushed and stirred in ether (200 mL). Collection of the solid by filtration and drying afforded the title compound (645 g), m.p. 37–39° C. Mass spectrum (+FAB, [M+H]$^+$) m/z 192. $^1$H-NMR (DMSO-d$_6$; 400 MHz): $\delta$10.45 (s, 1H), 4.36 (s, 2H), 4.12 (q, 2H), 4.05 (q, 2H), 1.19 (t, 3H), and 1.18 ppm (t, 3H).

Anal. for $C_7H_{13}NO_5$: Calcd.: C, 43.98; H, 6.85; N, 7.33. Found: C, 43.99; H, 6.75; N, 7.52.

Step 3

Ethyl N-methyl N-ethoxy carbonyl aminooxy acetate (4, R=Et, R$_1$=Me)

The mixture of Ethyl N-Ethoxy carbonyl aminooxy acetate (306 g), methyl iodide (455 g), potassium carbonate (400 g) and ethanol (500 mL) was heated at reflux for 3 hours, stirred at ambient temperature for 1 hours then filtered. The filtrate was evaporated to dryness. The residue was dissolved in ethyl acetate (1200 mL) and washed with water (3×700 mL). The organic phase was dried over anhydrous magnesium sulfate and evaporated to give (290.5 g) of ethyl N-methyl N-ethoxy carbonyl aminooxy acetate (4) as an oil. Mass spectrum (El, M.$^+$) m/z 205. $^1$H-NMR (DMSO-d$_6$; 400 MHz): $\delta$4.49 (s, 2H), 4.14 (q, 2H), 4.10 (q, 2H), 3.13 (s, 3H), and 1.20 ppm (dt, 6H).

Step 4

N-methyl aminooxy acetic acid hydrochloride (5, R$_1$=Me)

A mixture of ethyl N-methyl N-ethoxy carbonyl aminooxy acetate (280 g), hydrochloric acid (350 mL), and water (150 mL) was heated at reflux for 45 minutes then evaporated to dryness under vacuum. The mixture was treated with acetonitrile (200 mL) then evaporated to dryness. The title compound (170 g) was obtained as a semi solid. Mass spectrum (El, M.$^+$) m/z 105. $^1$H-NMR (DMSO-d$_6$; 400 MHz): $\delta$13–11 (br.s, 1H), 4.71 (s, 2H), and 2.8 (s, 3H).

Anal. for $C_3H_7NO_3$. HCl: Calcd.: C, 25.45; H, 5.70; N, 9.89. Found: C, 25.52; H, 5.93; N, 10.08.

N-Ethyl aminooxy acetic acid hydrochloride (5, R$_1$=Et)

The title compound was prepared as described in steps 1 to 4 of procedure A and substituting ethyl iodide for methyl iodide in step 3. $^1$H-NMR (DMSO-d$_6$; 300 MHz): $\delta$5.75 (s, 2H), 3.14 (q, 2H), and 1.15 ppm (t, 3H).

Procedure B

Step 1

Ethyl aminooxy acetate (2a, R=Et)

Ethyl Aminooxy acetate hydrochloride (2, R=Et) was prepared as described in step 1 of procedure A. The hydrochloride salt (24 g) was dissolved in water (100 mL). The solution was saturated with sodium bicarbonate and extracted with ethyl acetate (2–200 mL). The organic extract was washed with brine (100 mL), and dried over anhydrous magnesium sulfate. Evaporation of the solvent afforded the title compound (15.8 g) as an oil. $^1$H-NMR (DMSO-d$_6$; 300 MHz): $\delta$6.28 (s, 2H), 4.12 (s, 2H), 4.10 (q, 2H), and 1.20 ppm (t, 3H).

Step 2

Ethyl methyleneiminoxy acetate (3a, R=Et, R$_2$=R$_3$=H)

The mixture of ethyl Aminooxy acetate (11.9 g), paraformaldehyde (3.0 g) and ethanol (100 mL) was heated at reflux for three hours. The reaction mixture was cooled to ambient temperature then filtered to remove the undissolved solid. Evaporation of the solvent afforded 12 g of the title compound as an oil; $^1$H-NMR (DMSO-d$_6$; 400 MHz): $\delta$7.16 (d, 1H), 6.69 (d, 1H), 4.63 (s, 2H), 4.13 (q, 2H), and 1.20 ppm (t, 3H).

Step 3

Ethyl N-methyl aminooxy acetate (a, R=Et, R$_1$=Me)

To a stirring solution of ethyl methyleneiminoxy acetate (11.8 g) in ethanol (75 mL) was added sodium cyanoborohydride (11.3 g). Ethanolic hydrogen chloride was then added to bring the pH to 1–2. The reaction mixture was stirred for 3 hours then evaporated to dryness. The residue was dissolved in ether (400 mL) and water (300 mL). The mixture was saturated with solid sodium bicarbonate. The organic phase was washed with brine (200 mL), and dried over anhydrous magnesium sulfate. Evaporation of the solvent afforded 7.0 g of the title compound as an oil. Mass spectrum (El, M.$^+$) m/z 133. $^1$H-NMR (DMSO-d$_6$; 300 MHz): $\delta$6.84 (s, 1H), 4.15 (s, 2H), 4.10 (q, 2H), 2.53 (s, 3H), and 1.20 ppm (t, 3H).

Step 4

N-methyl aminooxy acetic acid hydrochloride (5, R$_1$=Me)

Ethyl N-methyl aminooxy acetate (5 g) was dissolved in ethanol (50 mL). A solution of potassium hydroxide (2 g) in water (10 mL) was added. The mixture was stirred at ambient temperature for 16 hours. The solvent was evaporated under vacuum. The residue was treated with 2N HCl (30 ml) and evaporated to dryness. The residue was stirred in ethyl acetate. The mixture was decanted. Drying under vacuum afforded the title compound (4.7 g) as a semi solid. Mass spectrum (El, M.$^+$) m/z 105. $^1$H-NMR (DMSO-d$_6$; 400 MHz): $\delta$13–11 (br.s, 1H), 4.71 (s, 2H), and 2.8 ppm (s, 3H).

Following steps 1 to 4 as described in procedure B and using the appropriate aldehydes or ketones, various N-alkyl aminooxy acetic acids were prepared.

EXAMPLE 1

4-(4-Chloro-2-methylphenyl)-2-methyl-3-thioxo-[1,2,4]oxadiazinan-5-one

A mixture of 4-chloro-2-methylphenyl-isothiocyanate (12.8 g), N-methyl aminooxy acetic acid hydrochloride (10 g), triethylamine (7.5 g) and chloroform (100 mL) was heated at reflux for one hour, stirred at ambient temperature for one hour, then evaporated to dryness. The residue was dissolved in ethyl acetate (200 mL) and extracted with sodium bicarbonate saturated solution (2×200 mL). The aqueous extract was acidified with 6N HCl and extracted with ethyl acetate (2×300 mL). The organic phase was washed with water (200 mL), dried over anhydrous magnesium sulfate and evaporated to dryness to give 13.9 g of [[[[(4-Chloro-2-methylphenyl)amino]thioxomethyl]methylamino]oxy]acetic acid as a solid, m.p. 110–113° C. Mass spectrum (El, M.$^+$) m/z 288/290. $^1$H-NMR (DMSO-d$_6$; 400 MHz) $\delta$13.20 (br s, 1H), 10.12 (s, 1H), 7.34–7.19 (m, 3H), 4.69 (q, 2H), 3.55 (s, 3H), and 2.17 ppm (s, 3H).

Anal. for $C_{11}H_{13}ClN_2O_3S$: Calcd.: C, 45.76; H, 4.54; N, 9.70. Found: C, 45.55; H, 4.41; N, 9.71.

The acid (26.5 g) was dissolved in benzene (250 mL). Phosphorus pentachloride (19.2 g) was added in portions. The mixture was heated at reflux for one half hour then evaporated to dryness. The residue was dissolved in ethyl acetate (500 mL) and washed with sodium bicarbonate saturated solution (2×300 mL) then with brine (300 mL). The organic phase was dried over anhydrous magnesium sulfate and evaporated to dryness. The residue was chromatographed on silica gel (40% methylene chloride in hexane). The title compound (12.8 g) was obtained as a solid, m.p. 141–143° C. Mass spectrum (El, M.$^+$) m/z 270/272. $^1$H-NMR (DMSO-d$_6$; 400 MHz) δ7.41 (d, 1H), 7.31 (dd, 1H), 7.16 (d, 1H), 5.11 (ABq, 2H), 3.68 (s, 3H), and 2.04 ppm (s, 3H).

Anal. for $C_{11}H_{11}ClN_2O_2S$: Calcd.: C, 48.80; H, 4.10; N, 10.35. Found: C, 48.57; H, 4.02; N, 10.31.

EXAMPLE 2

4-Benzhydryl-2-methyl-3-thioxo-[1,2,4]oxadiazinan-5-one

A mixture of benzhydryl-isothiocyanate (13.75 g), N-methyl aminooxy acetic acid hydrochloride (8.6 g), triethylamine (16 g) and chloroform (200 mL) was heated at reflux for three hours, stirred at ambient temperature for one hour. The mixture was diluted with chloroform (200 mL) and washed with 2N HCl (2×300 mL) then with water (300 mL). The organic phase was dried over anhydrous magnesium sulfate and evaporated to dryness to give a solid. The solid was stirred in ether (200 mL) and filtered to give 18.8 g of [[[[(benzhydryl)amino]thioxomethyl]methylamino]oxy]acetic acid as a white solid, m.p. 160–162° C. Mass spectrum (–FAB, [M–H]$^-$) m/z 329. $^1$H-NMR (DMSO-d$_6$; 400 MHz) δ13.55 (br s, 1H), 9.75 (d, 1H), 7.35–7.23 (m, 10H), 6.63 (d, 1H), 4.63 (s, 2H), and 3.42 ppm (s, 3H).

Anal. for $C_{17}H_{18}N_2O_3S$: Calcd.: C, 61.8; H, 5.49; N, 8.48. Found: C, 61.72; H, 5.28; N, 8.45.

The acid (15.5 g) was dissolved in benzene (200 mL). Phosphorus pentachloride (9.8 g) was added in portions. The mixture was heated at reflux for one half hour then evaporated to dryness. The residue was dissolved in ethyl acetate (400 mL) and washed with sodium bicarbonate saturated solution (2×300 mL) then with water (300 mL). The organic phase was dried over anhydrous magnesium sulfate and evaporated to dryness. The residue was chromatographed on silica gel (40% methylene chloride in hexane). The title compound (4.8 g) was obtained as a solid, m.p. 152–154° C. Mass spectrum (El, M.$^+$) m/z 312. $^1$H-NMR (DMSO-d$_6$; 400 MHz) δ7.68 (s, 1H), 7.35–7.23 (m,10H), 4.94 (ABq, 2H), and 3.73 ppm (s, 3H).

Anal. for $C_{17}H_{16}N_2O_2S$: Calcd.: C, 65.36; H, 5.16; N, 8.97. Found: C, 65.33; H, 5.09; N, 9.08.

EXAMPLE 3

4-(5-Chloro-2-methylphenyl)-2-methyl-3-thioxo-[1,2,4]oxadiazinan-5-one

A mixture of 5-chloro-2-methylphenyl-isothiocyanate (36.7 g), N-methyl aminooxy acetic acid hydrochloride (28.3 g), triethylamine (50 g) and chloroform (300 mL) was heated at reflux for one hour, stirred at ambient temperature for one hour, then evaporated to dryness. The residue was dissolved in ethyl acetate (700 mL) and washed with 2N HCl (3×300 mL) then with water (300 mL). The organic phase was dried over anhydrous magnesium sulfate and evaporated to dryness affording (48 g) of [[[[(5-Chloro-2-methylphenyl)amino]thioxomethyl]methylamino]oxy]acetic acid as a semi solid. $^1$H-NMR (DMSO-d$_6$; 300 Mhz) δ12.8 (br s, 1H), 10.15 (s, 1H), 7.35–7.20 (m, 3H), 4.62 (s, 2H), 3.56 (s, 3H), and 2.18 ppm (s, 3H). The acid (48 g) was dissolved in benzene (300 mL). Phosphorus pentachloride (42 g) was added in portions. The mixture was heated at reflux for one half hour then evaporated to dryness. The residue was dissolved in ethyl acetate (500 mL) and washed with sodium bicarbonate saturated solution (2×300 mL) then with water (300 mL). The organic phase was dried over anhydrous magnesium sulfate and evaporated to dryness. The residue was chromatographed on silica gel (10% ethyl acetate in hexane). Crystallization from ethyl acetate/hexane afforded the title compound (18 g) as a solid, m.p. 100–102° C. Mass spectrum (El, M.$^+$) m/z 270/272. $^1$H-NMR (CDCl$_3$; 400 MHz) δ7.32 (d, 1H), 7.24 (d, 1H), 7.14 (s, 1H), 4.84 (ABq, 2H), 3.74 (s, 3H), and 2.13 ppm (s, 3H).

Anal. for $C_{11}H_{11}ClN_2O_2S$: Calcd.: C, 48.8; H, 4.1; N, 10.35. Found: C, 48.92; H, 3.98; N, 10.42.

EXAMPLE 4

4-(5-Chloro-2-methylphenyl)-2-ethyl-3-thioxo-[1,2,4]oxadiazinan-5-one

A mixture of 5-chloro-2-methylphenyl-isothiocyanate (9.18 g), N-methyl aminooxy acetic acid hydrochloride (7.78 g), triethylamine (20 g) and chloroform (200 mL) was heated at reflux for one hour, stirred at ambient temperature for one hour, then evaporated to dryness. The residue was dissolved in ethyl acetate (400 mL) and washed with 2N HCl (2×200 mL) then with water (200 mL). The organic phase was dried over anhydrous magnesium sulfate and evaporated to dryness The residue (8 g) was dissolved in benzene (150 mL). Phosphorus pentachloride (7 g) was added in portions. The mixture was heated at reflux for one hour then evaporated to dryness. The residue was dissolved in ethyl acetate (300 mL) and washed with sodium bicarbonate saturated solution (2×200 mL) then with water (200 mL). The organic phase was dried over anhydrous magnesium sulfate and evaporated to dryness. The residue was chromatographed on silica gel (10–20% ethyl acetate in hexane). Crystallization from ethyl acetate/hexane afforded the title compound (2.1 g) as a solid, m.p. 119–121° C. Mass spectrum (El, M.$^+$) m/z 282/284. $^1$H-NMR (CDCl$_3$; 400 MHz) δ7.32 (d, 1H), 7.23 (d, 1H), 7.13 (s, 1H), 4.81 (ABq, 2H), 4.26 (m, 2H), 2.13 (s, 3H), and 1.40 ppm (t, 3H).

Anal. for $C_{12}H_{13}ClN_2O_2S$: Calcd.: C, 50.61; H, 4.6; N, 9.84. Found: C, 50.55; H, 4.40; N, 9.88.

EXAMPLE 5

4-Indan-5-yl-2-methyl-3-thioxo-[1,2,4]oxadiazinan-5-one

A mixture of 5-indanyl-isothiocyanate (18.5 g), N-methyl aminooxy acetic acid hydrochloride (16.2 g), triethylamine (25 g) and chloroform (150 mL) was heated at reflux for one half hour, stirred at ambient temperature for one hour, then evaporated to dryness. The residue was dissolved in ethyl acetate (500 mL) and washed with 2N HCl (2×400 mL) then with water (400 mL). The organic phase was dried over anhydrous magnesium sulfate and evaporated to dryness affording (31.3 g) of [[[[(5-indanyl)amino]thioxomethyl]methylamino]oxy]acetic acid as an oil. $^1$H-NMR (DMSO-d$_6$; 300 MHz) δ13.1 (br s, 1H), 10.5 (s, 1H), 7.38 (s, 1H), 7.18 (m, 2H), 4.62 (s, 2H), 3.50 (s, 3H), 2.82 (m, 4H), and 2.03 ppm (m, 2H). The acid (26.1 g) was dissolved in benzene (200 mL). Phosphorus pentachloride (25 g) was added in portions. The mixture was heated at reflux for one half hour then evaporated to dryness. The residue was dissolved in ethyl acetate (400 mL) and washed with sodium bicarbonate saturated solution (2×300 mL) then with water (300 mL). The organic phase was dried over anhydrous magnesium sulfate and evaporated to dryness. The residue was chromatographed on silica gel (10% ethyl acetate in hexane). Crystallization from ether afforded the title compound (4.3 g) as a solid, m.p. 135–137° C. Mass spectrum (El, M.$^+$) m/z 262. $^1$H-NMR (CDCl$_3$; 400 MHz) δ7.31 (d, 1H), 7.04 (s, 1H), 6.96 (d, 1H), 4.84 (ABq, 2H), 3.75 (s, 3H), 2.96 (t, 4H), and 2.11 ppm (m, 2H).

Anal. for $C_{13}H_{14}N_2O_2S$: Calcd.: C, 59.52; H, 5.38; N, 10.68. Found: C, 59.56; H, 5.42; N, 10.83.

EXAMPLE 6

4-(2,5-Dimethylphenyl)-2-methyl-3-thioxo-[1,2,4]oxadiazinan-5-one

A mixture of 2,5-dimethylphenyl-isothiocyanate (16.3 g), N-methyl aminooxy acetic acid hydrochloride (15.55 g), triethylamine (30 g) and chloroform (250 mL) was heated at reflux for one hour, stirred at ambient temperature for one hour, then evaporated to dryness. The residue was dissolved in ethyl acetate (500 mL) and washed with 2N HCl (2×200 mL) then with water (200 mL). The organic phase was dried over anhydrous magnesium sulfate and evaporated to dryness affording (25 g) of [[[[(2,5-dimethylphenyl)amino]thioxomethyl]methylamino]oxy]acetic acid as an oil. $^1$H-NMR (DMSO-d$_6$; 300 Mhz) δ13.25 (br s, 1H), 10.08 (s, 1H), 7.15–6.94 (m, 3H), 4.62 (s, 2H), 3.52 (s, 3H), 2.24 ppm (s, 3H and 2.10 ppm (s, 3H). The acid (24.1 g) was dissolved in benzene (250 mL). Phosphorus pentachloride (18.7 g) was added in portions. The mixture was heated at reflux for one half hour then evaporated to dryness. The residue was dissolved in ethyl acetate (600 mL) and washed with sodium bicarbonate saturated solution (2×300 mL) then with water (300 mL). The organic phase was dried over anhydrous magnesium sulfate and evaporated to dryness. The residual oily substance crystallized upon standing. The solid mass was stirred in methanol (100 mL). The solid was collected by filtration and air dried to give the title compound (11.2 g), m.p. 104–106° C. Mass spectrum (El, M.$^+$) m/z 250. $^1$H-NMR (CDCl$_3$; 400 MHz) δ7.21–7.17 (m, 2H), 6.92 (s, 1H), 4.84 (ABq, 2H), 3.75 (s, 3H), 2.35 (s, 3H), and 2.12 ppm (s, 3H).

Anal. for $C_{12}H_{14}N_2O_2S$: Calcd.: C, 57.58; H, 5.64; N, 11.19. Found: C, 57.48; H, 5.63; N, 11.23.

EXAMPLE 7

4-(2-Chloro-6-methylphenyl)-2-methyl-3-thioxo-[1,2,4]oxadiazinan-5-one

A mixture of 2-chloro-6-methylphenyl-isothiocyanate (18.3 g), N-methyl aminooxy acetic acid hydrochloride (15.5 g), triethylamine (30 g) and chloroform (300 mL) was heated at reflux for one hour, stirred at ambient temperature for one hour, then evaporated to dryness. The residue was dissolved in ethyl acetate (500 mL) and washed with 2N HCl (2×300 mL) then with water (300 mL). The organic phase was dried over anhydrous magnesium sulfate and evaporated to dryness affording (28 g) of [[[[(2-Chloro-6-ethylphenyl)amino]thioxomethyl]methylamino]oxy]acetic acid as a semi solid. $^1$H-NMR (DMSO-d$_6$; 300 Mhz) δ12.8 (br s, 1H), 10.04 (s, 1H), 7.38–7.20 (m, 3H), 4.61 (s, 2H), 3.58 (s, 3H), and 2.20 ppm (s, 3H). The acid (26.8 g) was dissolved in benzene (300 mL). Phosphorus pentachloride (18 g) was added in portions. The mixture was heated at reflux for one half hour then evaporated to dryness. The residue was dissolved in ethyl acetate (500 mL) and washed with sodium bicarbonate saturated solution (2×300 mL) then with water (300 mL). The organic phase was dried over anhydrous magnesium sulfate and evaporated to dryness. Crystallization from ethanol afforded the title compound (10.5 g) as a solid, m.p. 176–178° C. Mass spectrum (ESI, [M+H]$^+$) m/z 271/273. $^1$H-NMR (CDCl$_3$; 400 MHz) δ7.37 (d, 1H), 7.29 (t, 1H), 7.22 (d, 1H), 4.86 (ABq, 2H), 3.76 (s, 3H), and 2.21 ppm (s, 3H).

Anal. for $C_{11}H_{11}ClN_2O_2S$: Calcd.: C, 48.8; H, 4.1; N, 10.35. Found: C, 48.79; H, 3.92; N, 10.39.

EXAMPLE 8

4-(2-Isopropylphenyl)-2-methyl-3-thioxo-[1,2,4]oxadiazinan-5-one

A mixture of 2-isopropylphenyl-isothiocyanate (17.7 g), N-methyl aminooxy acetic acid hydrochloride (14.2 g), triethylamine (20 g) and chloroform (300 mL) was stirred at ambient temperature for two hour, then evaporated to dryness. The residue was dissolved in ethyl acetate (400 mL) and washed with 2N HCl (2×200 mL) then with water (100 mL). The organic phase was dried over anhydrous magnesium sulfate and evaporated to dryness affording (21 g) of [[[[(2-isopropylphenyl)amino]thioxomethyl]methylamino]oxy]acetic acid as an oil. $^1$H-NMR (DMSO-d$_6$; 300 Mhz) δ13.0 (br s, 1H), 10.15 (s, 1H), 7.42–7.05 (m, 4H), 4.63 (s, 2H), 3.58 (s, 3H), 3.08 (m, 1H), and 1.15 ppm (d, 6H). The acid (20 g) was dissolved in benzene (200 mL). Phosphorus pentachloride (14.7 g) was added in portions. The mixture was heated at reflux for one half hour then evaporated to dryness. The residue was dissolved in ethyl acetate (700 mL) and washed with sodium bicarbonate saturated solution (3×400 mL) then with water (300 mL). The organic phase was dried over anhydrous magnesium sulfate and evaporated to dryness. The residue was chromatographed on silica gel (10–50% methylene chloride in hexane). The title compound (12.8 g) was obtained as a solid, m.p. 98–101° C. Mass spectrum (El, M.$^+$) m/z 264. $^1$H-NMR (CDCl$_3$; 400 MHz) δ7.37 (m, 2H), 7.22 (t, 1H), 7.06 (d, 1H), 5.12 (q, 2H), 3.69 (s, 3H), 2.69 (m, 1H), 1.15 (d, 3H), and 1.04 ppm (d, 3H).

Anal. for $C_{13}H_{16}N_2O_2S$: Calcd.: C, 59.07; H, 6.10; N, 10.60. Found: C, 59.18; H, 5.88; N, 10.82.

EXAMPLE 9

4-(4-tert-Butylphenyl)-2-methyl-3-thioxo-[1,2,4]oxadiazinan-5-one

A mixture of 4-tert-butylphenyl-isothiocyanate (10.8 g), N-methyl aminooxy acetic acid hydrochloride (8.0 g), triethylamine (14 g) and chloroform (300 mL) was heated at reflux for three hours, then evaporated to dryness. The residue was treated with 2N HCl (300 mL) and the mixture was stirred for fifteen minutes. The solid was collected by filtration, washed with water and dried to give (16.8 g) of [[[[(4-tert-butylphenyl)amino]thioxomethyl]methylamino]oxy]acetic acid. $^1$H-NMR (DMSO-d$_6$; 300 Mhz) δ13.5 (br s, 1H), 10.48 (s, 1H), 7.48–7.32 (m, 4H), 4.62 (s, 2H), 3.52 (s, 3H), and 1.28 ppm (s, 9H). The acid (14.8 g) was dissolved in benzene (200 mL). Phosphorus pentachloride (10.4 g) was added in portions. The mixture was heated at reflux for one half hour then evaporated to dryness. The residue was dissolved in ethyl acetate (600 mL) and washed with sodium bicarbonate saturated solution (2×400 mL) then with water (400 mL). The organic phase was dried over anhydrous magnesium sulfate and evaporated to dryness. The residue was chromatographed on silica gel (40% methylene chloride in hexane). The title compound (9.1 g) was obtained as a solid, m.p. 168–170° C. Mass spectrum (El, M.+) m/z 276. $^1$H-NMR (DMSO-d$_6$; 400 MHz) δ7.45 (d, 2H), 7.09 (d, 2H), 5.06 (s, 2H), 3.68 (s, 3H), and 1.30 ppm (s, 9H).

Anal. for $C_{14}H_{18}N_2O_2S$: Calcd.: C, 60.41; H, 6.54; N, 10.06. Found: C, 60.67; H, 6.54; N, 10.18.

EXAMPLE 10

4-(4-Phenoxyphenyl)-2-methyl-3-thioxo-[1,2,4]oxadiazinan-5-one

A mixture of 4-phenoxyphenyl-isothiocyanate (11.35 g), N-methyl aminooxy acetic acid hydrochloride (7.1 g), triethylamine (10.5 g) and chloroform (300 mL) was heated at reflux for three hours, then evaporated to dryness. The residue was dissolved in ethyl acetate (600 mL) and washed with 2N HCl (2×300 mL) then with water (300 mL). The organic phase was dried over anhydrous magnesium sulfate and evaporated to dryness to give (16.8 g) of [[[[(4-phenoxyphenyl)amino]thioxomethyl]methylamino]oxy]acetic acid as an oil. $^1$H-NMR (DMSO-d$_6$; 300 Mhz) δ13.10 (br s, 1H), 10.50 (s, 1H), 7.50 (m, 2H), 7.38 (m, 2H), 7.12 (t, 1H), 6.98 (m, 4H), 4.63 (s, 2H), and 3.52 ppm (s, 3H). The acid (16.8 g) was dissolved in benzene (300 mL). Phosphorus pentachloride (10.4 g) was added in portions. The mixture was heated at reflux for one half hour then evaporated to dryness. The residue was dissolved in ethyl acetate (600 mL) and washed with sodium bicarbonate saturated solution (2×300 mL) then with water (300 mL). The organic phase was dried over anhydrous magnesium sulfate and evaporated to dryness. The residue was chromatographed on silica gel (40% methylene chloride in hexane). The title compound (8.6 g) was obtained as a solid, m.p. 159–160° C. Mass spectrum (El, M.+) m/z 314. $^1$H-NMR (DMSO-d$_6$; 400 MHz) δ7.43 (m, 2H), 7.19 (m, 3H), 7.09 (m, 2H), 7.00 (m, 2H), 5.07 (s, 2H), and 3.68 ppm (s, 3H).

Anal. for $C_{16}H_{14}N_2O_2S$: Calcd.: C, 61.13; H, 4.49; N, 8.91. Found: C, 61.14; H, 4.38; N, 8.80.

EXAMPLE 11

4-(5-Chloro-2-methoxyphenyl)-2-methyl-3-thioxo-[1,2,4]oxadiazinan-5-one

A mixture of 5-chloro-2-methoxyphenyl-isothiocyanate (11.45 g), N-methyl aminooxy acetic acid hydrochloride (8.15 g), triethylamine (20 g) and chloroform (250 mL) was heated at reflux for three hours, then evaporated to dryness. The residue was dissolved in ethyl acetate (400 mL) and washed with 2N HCl (2×300 mL) then with water (300 mL). The organic phase was dried over anhydrous magnesium sulfate and evaporated to dryness to give (17.1 g) of [[[[(5-chloro-2-metoxyphenyl)amino]thioxomethyl]methylamino]oxy]acetic acid as an oil that solidifies upon standing. The acid (15.2 g) was dissolved in benzene (200 mL). Phosphorus pentachloride (10.4 g) was added in portions. The mixture was heated at reflux for one half hour then evaporated to dryness. The residue was dissolved in ethyl acetate (500 mL) and washed with sodium bicarbonate saturated solution (2×300 mL) then with water (300 mL). The organic phase was dried over anhydrous magnesium sulfate and evaporated to dryness. The residue was chromatographed on silica gel (40–60% methylene chloride in hexane). The title compound (5.1 g) was obtained as a solid, m.p. 189–191° C. Mass spectrum (El, M.+) m/z 286/288. $^1$H-NMR (DMSO-d$_6$; 400 MHz) δ7.44 (d, 1H), 7.31 (s, 1H), 7.14 (d, 1H), 5.06 (s, 2H), 3.73 (s, 3H), and 3.63 ppm (s, 3H).

Anal. for $C_{11}H_{11}ClN_2O_3S$: Calcd.: C, 46.08; H, 3.87; N, 9.77. Found: C, 46.01; H, 3.84; N, 9.59.

The present invention may be embodied in other specific forms without departing from the spirit and essential attributes thereof and accordingly, reference should be made to the appended claims, rather than to the foregoing specification, as indicating the scope of the invention.

What is claimed is:

1. An antiatherosclerotic compound of Formula I:

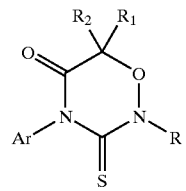

wherein:

R is lower alkyl, alkenyl of 2–6 carbon atoms, or alkynyl of 2–6 carbon atoms;

$R_1$ and $R_2$ are each independently hydrogen, alkyl, or aryl; and

Ar is phenyl, indanyl, benzhydryl, or phenyl substituted with one or more members of the group consisting of halogen, lower alkyl, perfluoroalkyl, lower alkoxy, perfluoroalkylalkoxy, dialkylamino, and aroyloxy; or a pharmaceutically acceptable salt thereof.

2. The antiatherosclerotic compound of claim 1 wherein:

R is alkyl;

$R_1$ and $R_2$ are each hydrogen; and

Ar is phenyl, indanyl, benzhydryl, or phenyl substituted with one or more members of the group consisting of halogen, alkyl, alkoxy, and aroyloxy.

3. The antiatherosclerotic compound of claim 1 which is 4-(5-Chloro-2-methylphenyl)-2-methyl-3-thioxo-1,2,4-oxadiazin-5-one.

4. The antiatherosclerotic compound of claim 1 which is 4-(5-Chloro-2-methylphenyl)-2-ethyl-3-thioxo-1,2,4-oxadiazin-5-one.

5. The antiatherosclerotic compound of claim 1 which is 4-(4-Chloro-2-methylphenyl)-2-methyl-3-thioxo-1,2,4-oxadiazin-5-one).

6. The antiatherosclerotic compound of claim 1 which is 4-(Indan-5-yl)-2-methyl-3-thioxo-1,2,4-oxadiazin-5-one.

7. The antiatherosclerotic compound of claim 1 which is 4-(2,5-Dimethylphenyl)-2-methyl-3-thioxo-1,2,4-oxadiazin-5-one.

8. The antiatherosclerotic compound of claim 1 which is 4-(6-Chloro-2-methylphenyl)-2-methyl-3-thioxo-1,2,4-oxadiazin-5-one.

9. The antiatherosclerotic compound of claim 1 which is 4-(2-Isopropylphenyl)-2-methyl-3-thioxo-1,2,4-oxadiazin-5-one.

10. The antiatherosclerotic compound of claim 1 which is 4-(Diphenylmethyl)-2-methyl-3-thioxo-1,2,4-oxadiazin-5-one.

11. The antiatherosclerotic compound of claim 1 which is 4-(4-t-Butylylphenyl)-2-methyl-3-thioxo-1,2,4-oxadiazin-5-one.

12. The antiatherosclerotic compound of claim 1 which is 4-(4-Phenoxyphenyl)-2-methyl-3-thioxo-1,2,4-oxadiazin-5-one.

13. The antiatherosclerotic compound of claim 1 which is 4-(5-Chloro-2-methoxyphenyl)-2-methyl-3-thioxo-1,2,4-oxadiazin-5-one.

14. A pharmaceutical composition comprising an antiatherosclerotic compound of the formula:

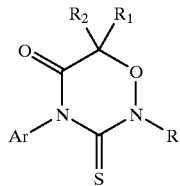

wherein
- R is lower alkyl, alkenyl of 2–6 carbon atoms or alkynyl of 2–6 carbon atoms;
- $R_1$ and $R_2$ are each independently hydrogen, alkyl or aryl; and
- Ar is phenyl, indanyl, benzhydryl, or phenyl substituted with one or more members of the group consisting of halogen, lower alkyl, penfluoroalkyl, lower alkoxy, perfluoroalkylalkoxy, dialkylamino and aroyloxy; as a pharmaceutically acceptable salt thereof and an inert carrier.

15. A method of treating atherosclerosis in a mammal in need thereof, which comprises administering to said mammal an anti-atherosclerotic effective amount of a compound of the formula:

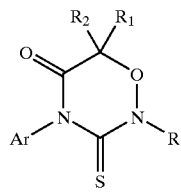

wherein:
- R is lower alkyl, alkenyl of 2–6 carbon atoms, or alkynyl of 2–6 carbon atoms;
- $R_1$ and $R_2$ are each independently hydrogen, alkyl, or aryl; and
- Ar is phenyl, indanyl, benzhydryl, or phenyl substituted with one or more members of the group consisting of halogen, lower alkyl, perfluoroalkyl, lower alkoxy, perfluoroalkylalkoxy, dialkylamino, and aroyloxy; as a pharmaceutically acceptable salt thereof.

* * * * *